United States Patent
Grundfest et al.

(10) Patent No.: US 11,857,373 B2
(45) Date of Patent: Jan. 2, 2024

(54) MULTI-FREQUENCY HARMONIC ACOUSTOGRAPHY FOR TARGET IDENTIFICATION AND BORDER DETECTION

(71) Applicant: THE REGENTS OF THE UNIVERSITY OF CALIFORNIA, Oakland, CA (US)

(72) Inventors: Warren S. Grundfest, Los Angeles, CA (US); Maie St. John, Los Angeles, CA (US); Ashkan Maccabi, Tarzana, CA (US); George Saddik, Newbury Park, CA (US); Zachary D. Taylor, Poway, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 488 days.

(21) Appl. No.: 16/373,777

(22) Filed: Apr. 3, 2019

(65) Prior Publication Data
US 2019/0293789 A1    Sep. 26, 2019

Related U.S. Application Data

(63) Continuation of application No. PCT/US2017/053709, filed on Sep. 27, 2017.
(Continued)

(51) Int. Cl.
*A61B 8/08* (2006.01)
*A61B 8/00* (2006.01)
(Continued)

(52) U.S. Cl.
CPC .............. *A61B 8/485* (2013.01); *A61B 8/085* (2013.01); *A61B 8/4494* (2013.01);
(Continued)

(58) Field of Classification Search
CPC ...... G01S 8/539; G01S 7/539; G01S 15/8906; G01S 15/8909; G01S 15/8911;
(Continued)

(56) References Cited

U.S. PATENT DOCUMENTS

| 5,467,767 A | 11/1995 | Alfano |
| 5,606,971 A | 3/1997 | Sarvazyan |

(Continued)

FOREIGN PATENT DOCUMENTS

| CN | 107072505 A | 8/2017 |
| JP | 2005504561 A | 2/2005 |

(Continued)

OTHER PUBLICATIONS

State Intellectual Property Office of the P.R.C., Office Action dated Aug. 3, 2021, related Chinese patent application No. 201880076496.7, pp. 1-9, English-language translation, pp. 10-18, claims examined, pp. 19-25.

(Continued)

*Primary Examiner* — Oommen Jacob
(74) *Attorney, Agent, or Firm* — O'BANION & RITCHEY LLP; John P. O'Banion

(57) ABSTRACT

A vibro-acoustography imaging system that generates a map of the mechanical response of a target to an acoustic radiation force, usually in low kHz range by a confocal geometry. The system generates two focused sinusoidal beams to produce a stress field at the beat frequency, which is a function of vibration and acoustic emissions field in terms of mechanical properties. A highly sensitive hydrophone is then used for detection of the acoustic emissions field, the amplitude of which may be correlated to the mechanical properties of the target tissue.

14 Claims, 12 Drawing Sheets

Related U.S. Application Data

(60) Provisional application No. 62/404,014, filed on Oct. 4, 2016, provisional application No. 62/403,776, filed on Oct. 4, 2016.

(51) Int. Cl.
  *B06B 1/06* (2006.01)
  *G01S 15/89* (2006.01)
  *G01S 7/52* (2006.01)

(52) U.S. Cl.
  CPC ........ *B06B 1/0622* (2013.01); *G01S 7/52038* (2013.01); *G01S 15/8913* (2013.01); *G01S 15/8922* (2013.01); *G01S 15/8952* (2013.01); *A61B 8/5207* (2013.01); *G01S 7/5203* (2013.01)

(58) Field of Classification Search
  CPC ............. G01S 15/8913; G01S 15/8915; G01S 15/8918; G01S 7/52038; B06B 1/0622; A61B 8/4483; A61B 8/4494; A61B 8/485; A61B 8/461
  See application file for complete search history.

(56) References Cited

U.S. PATENT DOCUMENTS

| | | | |
|---|---|---|---|
| 5,846,517 A * | 12/1998 | Unger | A61K 49/227 424/9.52 |
| 5,903,516 A | 5/1999 | Greenleaf | |
| 5,991,239 A | 11/1999 | Fatemi-Booshehri | |
| 6,438,258 B1 * | 8/2002 | Brock-Fisher | G01S 7/52038 382/128 |
| 6,984,209 B2 | 1/2006 | Hynynen | |
| 7,713,201 B2 | 5/2010 | Chen | |
| 7,753,847 B2 | 7/2010 | Greenleaf | |
| 7,785,259 B2 | 8/2010 | Zheng | |
| 8,043,217 B1 | 10/2011 | Rambod | |
| 8,659,975 B2 | 2/2014 | Greenleaf | |
| 9,833,634 B2 | 12/2017 | Bourke | |
| 10,041,883 B2 | 8/2018 | Grundfest | |
| 2001/0031922 A1 * | 10/2001 | Weng | A61N 7/02 600/439 |
| 2001/0051771 A1 * | 12/2001 | Bradley | G01S 15/895 600/443 |
| 2003/0067680 A1 | 4/2003 | Weinstein | |
| 2005/0004466 A1 | 1/2005 | Hynynen | |
| 2005/0096542 A1 | 5/2005 | Weng | |
| 2006/0079773 A1 * | 4/2006 | Mourad | A61B 8/00 600/438 |
| 2007/0038095 A1 | 2/2007 | Greenleaf | |
| 2008/0091125 A1 | 4/2008 | Owen | |
| 2009/0281422 A1 * | 11/2009 | Salama | A61B 5/05 600/430 |
| 2011/0130660 A1 | 6/2011 | Cloutier | |
| 2012/0130248 A1 * | 5/2012 | Fatemi | A61B 8/06 600/454 |
| 2012/0289827 A1 | 11/2012 | Ismail | |
| 2012/0296204 A1 | 11/2012 | Ismail | |
| 2012/0302892 A1 | 11/2012 | Lue | |
| 2013/0131488 A1 | 5/2013 | Zeng | |
| 2015/0053871 A1 | 2/2015 | Grundfest | |
| 2015/0060698 A1 | 3/2015 | Mozolowski | |
| 2015/0065871 A1 * | 3/2015 | Konofagou | A61B 8/4281 600/431 |
| 2015/0112197 A1 * | 4/2015 | Bharat | A61N 5/1077 600/438 |
| 2016/0139051 A1 | 5/2016 | Auner | |
| 2018/0088051 A1 | 3/2018 | Georgakoudi | |
| 2019/0293789 A1 * | 9/2019 | Grundfest | G01S 7/539 |
| 2020/0001114 A1 | 1/2020 | Bharat | |
| 2020/0323431 A1 | 10/2020 | St John | |

FOREIGN PATENT DOCUMENTS

| | | |
|---|---|---|
| JP | 2008279274 | 11/2008 |
| JP | 2008279274 A | 11/2008 |
| JP | 2009258746 A | 11/2009 |
| JP | 2010233843 A | 10/2010 |
| WO | 0243564 A2 | 6/2002 |
| WO | 03005446 A1 | 1/2003 |
| WO | 2011090792 A1 | 7/2011 |
| WO | 2018067355 | 4/2018 |
| WO | 2019089998 A1 | 5/2019 |

OTHER PUBLICATIONS

European Patent Office (EPO), "Communication—The extended European search report" dated Jul. 20, 2021, related EPO application No. 18872191.4, pp. 1-8, claims searched, pp. 9-12.

Japanese Patent Office (JPO), Notice of Reasons for Refusal dated Sep. 3, 2021, related Japanese patent application No. 2019-517934, pp. 1-4, English-language translation, pp. 5-8, claims examined, pp. 9-13.

Tajudeen, Bobby A. et al., "Dynamic Optical Contrast Imaging as a Novel Modality for Rapidly Distinguishing Head and Neck Squamous Cell Carcinoma from Surrounding Normal Tissue", Cancer, Tumor Imaging for Head and Neck Cancer, Cancer, Mar. 1, 2017, pp. 879-886, published online Oct. 20, 2016, Wiley Online Library (wileyonlinelibrary.com).

Jiang, Pei-Chi et al., "Quasi-real-time fluorescence imaging with lifetime dependent contrast", Journal of Biomedical Optics 16(8), 086001 (Aug. 2011), published online Aug. 31, 2011.

ISA/US, International Search Report and Written Opinion dated Jan. 18, 2019, related PCT international application No. PCT/US2018/058806, pp. 1-11, claims searched, pp. 12-18.

Sherman, Adria Jardeni, "Characterization and Optimization of a Normalized Fluorescence Lifetime Imaging System of Biological Samples", University of California, Los Angeles, Thesis, 2013, 90 pages.

Papour, Asael, "Analysis and Optimization of a Lifetime Fluorescence System to Detect Structural Protein Signatures in Varying Host Mediums for Rapid Biomedical Imaging", University of California, Los Angeles, Thesis, 2012, 78 pages.

European Patent Office (EPO), Communication (The extended European search report) dated May 8, 2020, related European patent application No. 17858912.3, pp. 1-12, claims searched, pp. 13-17.

ISA/US, International Search Report and Written Opinion dated Dec. 11, 2017, related PCT international applicatinon No. PCT/US2017/053709, pp. 1-14, claims searched, pp. 15-19.

Urban, Matthew W. et al., "Implementation of Vibro-Acoustography on a Clinical Ultrasound System", IEEE Transactions on Ultrasonics, Ferroelectrics, and Frequency Control, vol. 58, No. 6, Jun. 2011, pp. 1169-1181.

Fatemi, M. et al., "Vibro-acoustography: An imaging modality based on ultrasound-stimulated acoustic emission", Proceedings of the National Academy of Sciences of the United States of America, 1999. 96(12): p. 6603-6608.

Maccabi, A., et al., "An examination of the elastic properties of tissue mimicking phantoms using vibro-acoustography and a muscle motor system", Review of Scientific Instruments, 2016. 87(2): p. 024903, published online Feb. 24, 2016.

Maccabi, A., et al., "Ex vivo viscoelastic characterization of head and neck tissue abnormalities using ultrasound-stimulated vibro-acoustography (USVA)", in SPIE Medical Imaging. 2014, International Society for Optics and Photonics.

European Patent Office (EPO), Communication pursuant to Article 94(3) EPC dated Jan. 5, 2022, related European patent application No. 17858912.3, pp. 1-15, claims searched, pp. 16-20.

Israel Patent Office, Notification No. 26 issued Dec. 26, 2021, related Israel patent application No. 265763, pp. 1-3, English-language translation, pp. 4-6, claims examined, pp. 7-11.

Japanese Patent Office (JPO), Notice of Reasons for Refusal dated Sep. 6, 2022, related Japanese patent application No. 2020-523716, pp. 1-4, English-language translation, pp. 5-8, claims examined, pp. 9-14.

(56) References Cited

OTHER PUBLICATIONS

European Patent Office (EPO), Communication pursuant to Article 94(3) EPC dated Dec. 2, 2022, related European patent application No. 17858912.3, pp. 1-20, claims searched, pp. 21-26.

Intellectual Property India, Examination Report dated May 26, 2023, related Indian patent application No. 202017017805, Indian-English translated document pp. 1-9, with claims examined, pp. 10-15.

Jiang, Pei-Chi, et al., "Quasi-real-time fluorescence imaging with lifetime dependent contrast", Journal of Biomedical Optics, 16(8), Aug. 2011, pp. 1-10.

ISA/KR, Korean Intellectual Property Office (KIPO), official action dated Oct. 2, 2023, related Korean application No. 10-2020-7015037, Korean-language document, pp. 1-11, English-language translation, 12-25, with claims examined, 26-31.

European Patent Office (EPO), "Communication pursuant to Article 94(3)" dated Oct. 5, 2023, related EPO application No. 17 858 912.3, pp. 1-13, claims searched, pp. 14-17.

* cited by examiner

//patents
MULTI-FREQUENCY HARMONIC ACOUSTOGRAPHY FOR TARGET IDENTIFICATION AND BORDER DETECTION

CROSS-REFERENCE TO RELATED APPLICATIONS

This application claims priority to, and is a 35 U.S.C. § 111(a) continuation of, PCT international application number PCT/US2017/053709 filed on Sep. 27, 2017, incorporated herein by reference in its entirety, which claims priority to, and the benefit of, U.S. provisional patent application Ser. No. 62/404,014 filed on Oct. 4, 2016, incorporated herein by reference in its entirety, and which also claims priority to, and the benefit of, U.S. provisional patent application Ser. No. 62/403,776 filed on Oct. 4, 2016, incorporated herein by reference in its entirety.

The above-referenced PCT international application was published as PCT International Publication No. WO 2018/067355 A1 on Apr. 12, 2018, which publication is incorporated herein by reference in its entirety.

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to medical imaging, and more particularly to a vibro-acoustography (VA) system for non-invasive boundary detection of malignant and normal tissues.

2. Background Discussion

Changes in elasticity of soft tissues are closely related to tissue pathology. However, estimation of this mechanical parameter for tissue characterization remains difficult in clinical practice.

The current gold standard is palpation, which is a subjective static technique that determines the relative superficial change between proximal regions of varying stiffness. Other approaches include Optical coherence tomography (OCT), computed tomography (CT), and Magnetic Resonance Enterography (MRE). Pre-operative imaging with magnetic resonance imaging (MRI), CT, and ultrasound provide useful information but are difficult to apply in intra-operative setting. Ultrasound has a long history of intra-operative application but it also has its limitation. Note that lack of diagnostic efficacy renders these techniques sub-optimal for intra-operative use. Major limitations include, for example, low sensitivity, low contrast, no real-time images, false negatives, and low depth of penetration.

Thus, current tumor margin identification methodologies rely on tactile feedback and the experience of the surgeon to decide how much tissue to cut. This method is highly variable in both success and clinical outcome as too little tissue removal can lead to tumor recurrence and too much can lead to debilitating effects.

High incidence of metastases in patients with squamous cell carcinoma (SCC) is very common, and consequently depends heavily on complete surgical resection with negative margins. However, a significant challenge in the treatment is the complexity and the unfamiliarity of the surrounding regions around the malignancy. The primary goal of a surgical treatment is the complete removal of malignant cells while preserving the healthy tissues surrounding it. Thus, there is a pressing need for the use of a real-time, high-resolution imaging modality to accurately differentiate between healthy and malignant tissues. Currently, the most commonly used methods for estimating tumor boundaries are dye injections, conventional ultrasound, manual palpation, and OCT elastography. However, most of these techniques suffer from major limitations such as poor sensitivity and low specificity. Major factors such as contrast, sensitivity, and spatial resolution are critical system parameters for the determination of a boundary for diseased regions with highlighted borders; therefore, there is an acute need for a sensitive yet efficient imaging modality with the ability to rapidly and accurately provide a focal region with accurate boundaries.

BRIEF SUMMARY

This disclosure generally describes a vibro-acoustography (VA) system that is configured to provide multi-frequency harmonic acoustography for target identification and border detection.

In one embodoment, the system comprises a clinically versatile, compact vibro-acoustography (VA) system for non-invasive boundary detection of malignant and normal tissues in intra-operative applications. Current techniques, including palpation and elastography, suffer from subjectivity, limited specificity, and lack of depth of penetration, and, thus, are ineffective for real-time intra-operative use. VA has previously been used to image embedded objects in soft tissue with high contrast. However, in vivo compact VA systems have yet to be established for clinical use. As a first step in bringing compact quality VA imaging systems to the clinic, the technology of this disclosure focuses on simulations of a small footprint VA system with two orientations of confocal transducer for real-time (generally 30 seconds to one minute using common processing capabilities) systematic evaluation using different detection schemes.

Another aspect is a multi-phono acoustography system and method that uses focused ultrasonic beams at multiple frequencies to interrogate a target of interest and ascertain mechanical properties through detection and analysis of harmonics generated by the non-linear properties of the tissue. The non-linear properties may comprise a convolution of one or more of: tissue type, size, and adjacent tissue and unique to the physiologic or disease state of the tissue of interest.

The VA imaging system of the present description uses an imaging modality that generates a map of the mechanical response of a target to an acoustic radiation force, usually in low kHz range by a confocal geometry. By way of example, and not of limitation, according to an embodiment of the technology described in this disclosure, the system generates two focused sinusoidal beams at $f_1$ and $f_2$, where $f_2=f_1+\Delta f$ to produce a stress field at the beat frequency, which is a function of vibration and acoustic emissions field in terms of mechanical properties at Δf. A highly sensitive hydrophone is then used for detection of the acoustic emissions field, the amplitude of which may be correlated to the mechanical properties of the target tissue.

Another aspect is multi-phono acoustography system and method that uses focused ultrasonic beams at multiple frequencies to interogate a target of interest and ascertain mechanical properties through detection and analysis of harmonics generated by the non-linear properties of the tissue. The non-linear properties are a convolution of tissue type, size, and adjacent tissue and unique to the physiologic or disease state of the tissue of interest.

A further aspect is an acoustography system configured to allow the surgeon to achieve clear margins with minimal normal tissue removal thus maximizing the functional. The system uses the presence and relative strengths of the higher harmonics (spectral envelope) to create imaging contrast and unique identifying information. Spectral envelope processing provides a unique tool for medical imaging, as current methods do not provide for both contrast generation and tissue identification. The system may be used for non-destructive testing and/or evaluation Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
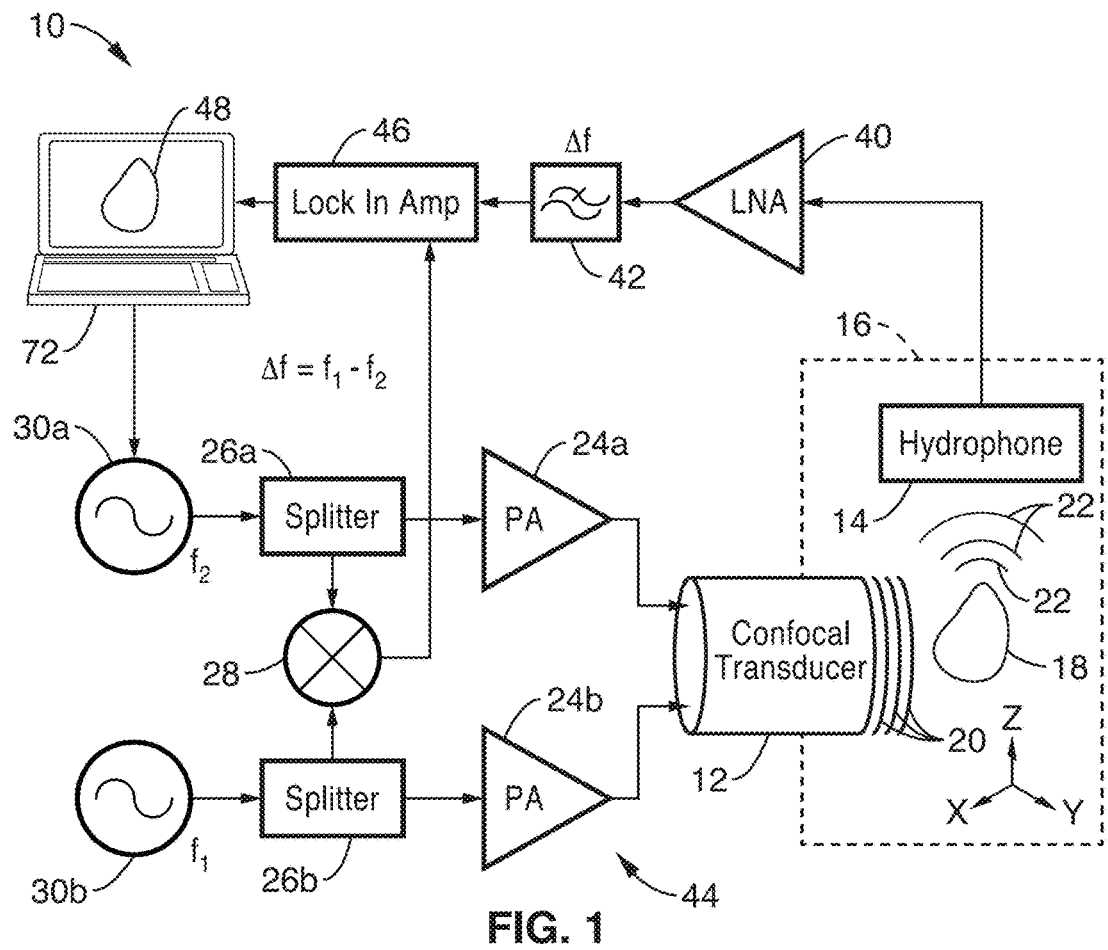
FIG. 1 shows a schematic diagram of a vibro-acoustography system in accordance with the present description.
Figure 2:
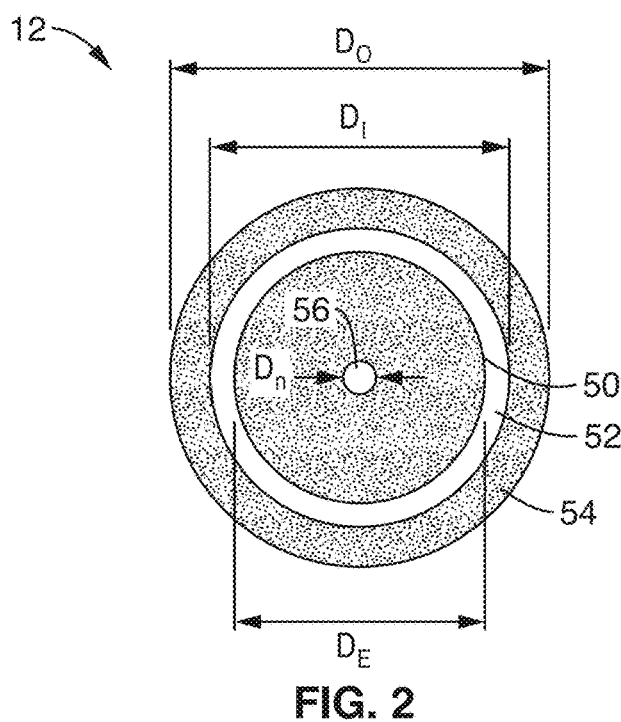
FIG. 2 shows a plan view of the confocal curved element of FIG. 1.

Described herein is an imaging modality, referred to herein as vibro-acoustography (VA), which uses ultrasound-based technology to identify materials. VA is a non-invasive imaging modality that uses the viscoelastic (i.e., mechanical) properties of targets to distinguish various material types within a region or volume of interest. The approach described herein relates directly to the mechanical properties of tissue through quantitative mathematical modeling. This allows for absolute quantitative measurement of tissue properties using the VA technology.

1. System Configuration

Referring to FIG. 1 through FIG. 8, in one embodiment a VA system 10 according to the presented technology includes a focused confocal transducer 12, which possesses a piezoelectric element and a compact hydrophone 14 for detection. Two pulse generators 30a and 30b supply two electrical sinusoidal waves, $f_1$ and $f_2$ (where $f_2=f_1+\Delta f$), to the transducer 12. Waves $f_1$ and $f_2$ are applied to the inner 50 and outer portions 54 of the piezoelectric element 12 (see FIG. 2) to emit two distinct acoustic waves $f_1$ and $f_2$ as waves 20 into the tissue 16 at the focal plane of the transducer 12. The two waves interfere at the focal plane within tissue or material 16 to vibrate the tissue 16, generating a third acoustic wave 22 in the kHz region of spectrum. This is energy transformation is accomplished as the target tissue 18 absorbs the energy and emits its own unique vibration at the difference frequency (Δf), as well as its harmonics, which is then recorded by the nearby compact hydrophone 14.

The signal received by the hydrophone 14 is then filtered and amplified with a Low Noise Amplifier (LNA) 40. The filtered signal 42 is then passed through a lock-in amplifier 46, and processed by a signal processor 72 (e.g., computer hardware processing circuit 78 and related software instructions 74, see FIG. 8) for absolute characterization. Detecting the acoustic responses not only generates contrast sufficient for image formation, but the acquired data enables for the quantitative characterization of material properties without reliance on reflection/attenuation of acoustic waves.

In a preferred embodiment, system 10 generates two unmodulated continuous wave (CW) ultrasonic beams (f1 and f2) at a slightly different frequencies in the low-MHz range to impose a low frequency kHz stress field (or beat frequency) 22. Each beam is generated by a coherent function generator (30a and 30b) and power amplifier 24a and 24b. The two amplified frequencies are then fed into a confocal transducer 12 with f1 coupled to the inner transducer ring 50 and f2 coupled to the outer ring 54. This produces two converging beams that overlap at the target of interest 18. Depending on the viscoelastic properties of the target 18, the generated radiation force will cause a portion or the entire tissue of interest to vibrate at the difference frequency $\Delta f = |f1-f2|$. Further, the combination of viscoelastic properties and tissue volumes result in mechanical non-linearities that describe the harmonic generation behavior. The result is a variation on the acoustic yield of the harmonics of $\Delta f$. This can be expressed as an infinite sum of integer multiples of the fundamental:

$$n_1*(\Delta f)+n_2*(2*\Delta f)+n_3*(3*\Delta f)+n_4*(4*\Delta f)+ \quad \text{Eq. 1.}$$

The presence and relative strengths of these harmonics form a unique tissue type identifier.

The acoustic harmonic emission of the tissue is detected by a hydrophone 14 located near the illuminated tissue. In a preferred embodiment shown in FIG. 2, the hydrophone 14 is disposed within a hole 56 at the center of the inner transducer element 50. While hole 56 is shown in the center of the inner transducer, it is appreciated that it may be positioned at any location within the device. In one configuration, the outer diameter $D_o$ of the outer transducer 54 is 45.04 mm, with an outer diameter $D_I$ of 30.86. The diameter $D_E$ of the inner transducer is sized smaller than $D_I$ (e.g. 28.56 mm) such that a gap 52 is formed between inner 50 and outer 54 transducers. Center hole 56 is sized (e.g. 2.7 mm) to receive hydrophone 14.

Figure 3:
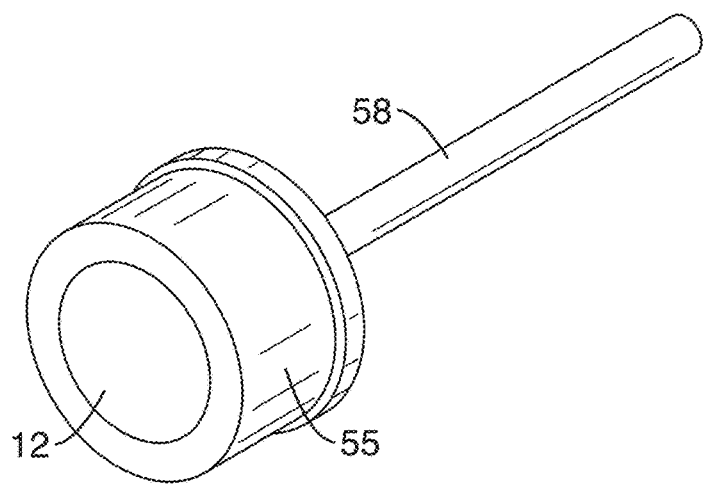
FIG. 3 shows a perspective view of the element of FIG. 2 and housing.

FIG. 3 shows a perspective view of the transducer 12 and housing 55 configured to concentrically receive transducer 12. An optical post 58 couples to the back of housing 55.

Figure 4A:
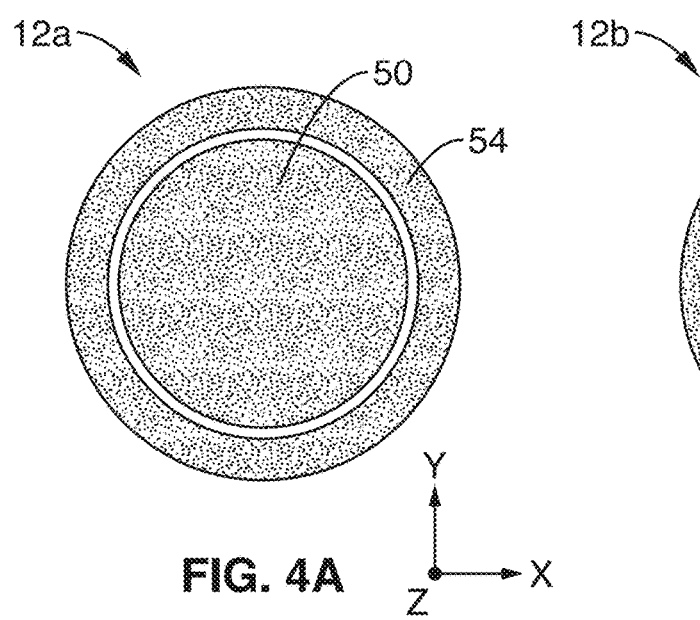
FIG. 4A and FIG. 4B show variations of the confocal curved element of FIG. 1.
Figure 4B:
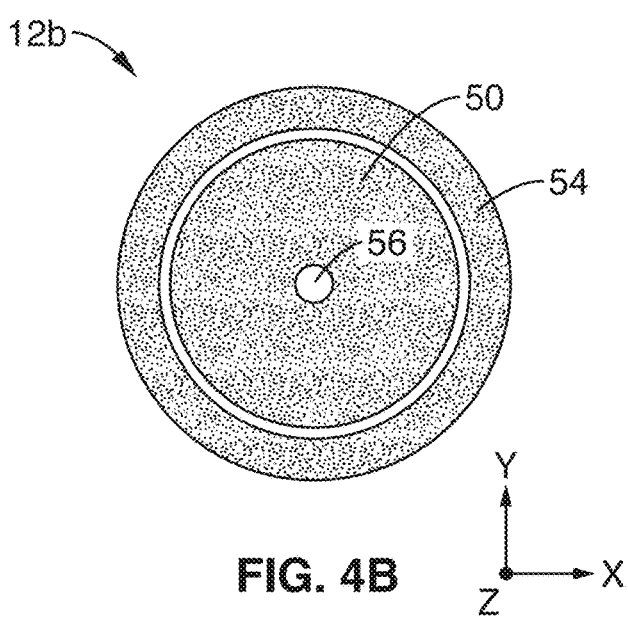

FIG. 4A and FIG. 4B show variations of the confocal curved element 12 of FIG. 1. FIG. 4A shows a transducer 12*a* with a solid inner transducer 54 disposed within outer transducer 54. FIG. 4B shows a transducer 12*b* with an inner transducer with center hole 56 in inner transducer 50, the hole 56 sized to receive hydrophone 14.

Figure 5:
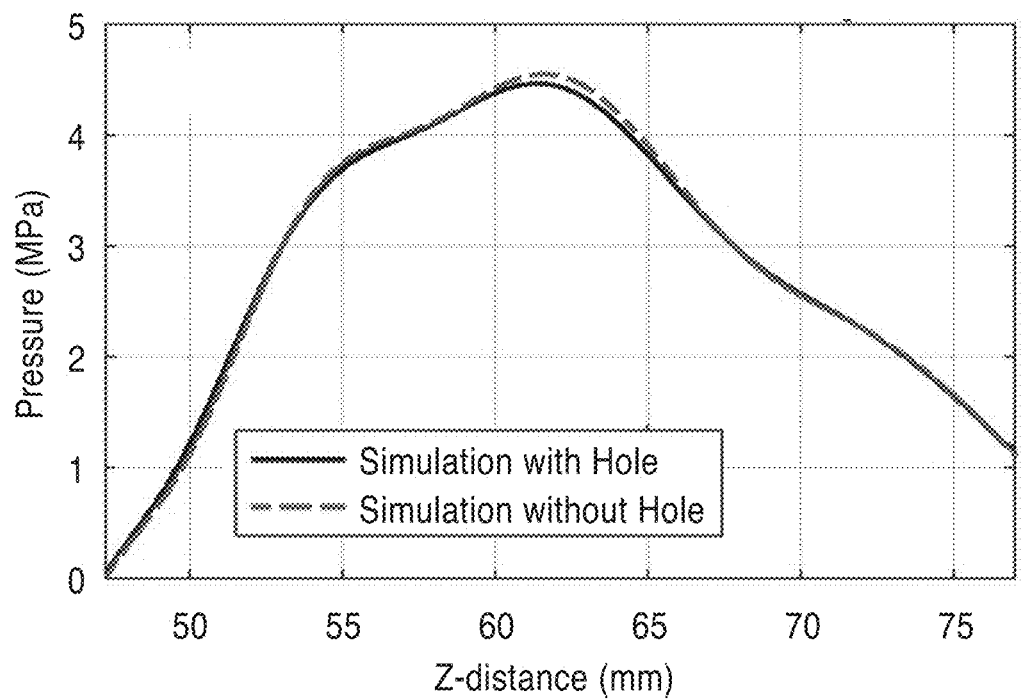
FIG. 5 shows a plot comparing beam profiles of the curved elements of FIG. 4A and FIG. 4B.

FIG. 5 shows a plot of a simulation comparing beam profiles of the curved elements 14*a*, and 14*b* of FIG. 4A and FIG. 4B, respectively. The z-axis envelope beam profile comparison shows an ROC of 60 mm. The inner transducer 50 had a frequency of 3.2 MHz and the outer transducer 54 had a frequency of 3.16 MHz for both cases.

Figure 6:
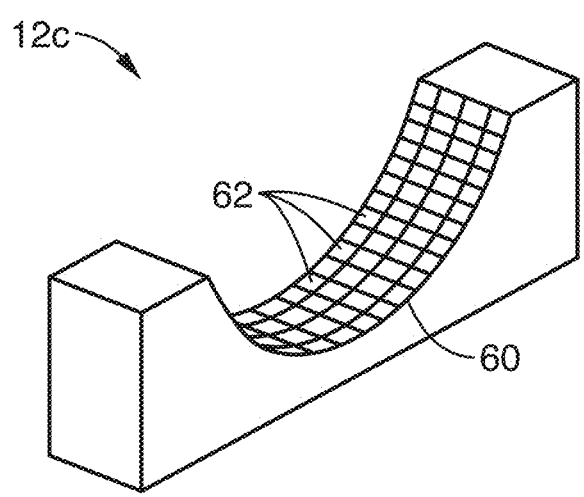
FIG. 6 is a perspective view of an alternative confocal phase-delayed array in accordance with the present description.

FIG. 6 shows an alternative embodiment of a curved transducer 12*c* having concave surface 60 and plurality or array of transducer elements 62, which may be used as a phase-delayed array. The array of transducer elements 62 allows for electrical beam steering (as opposed to mechanical beam steering), which allows for faster, instantaneous images. A hydrophone (not shown), may also be embedded within the array.

Figure 7A:
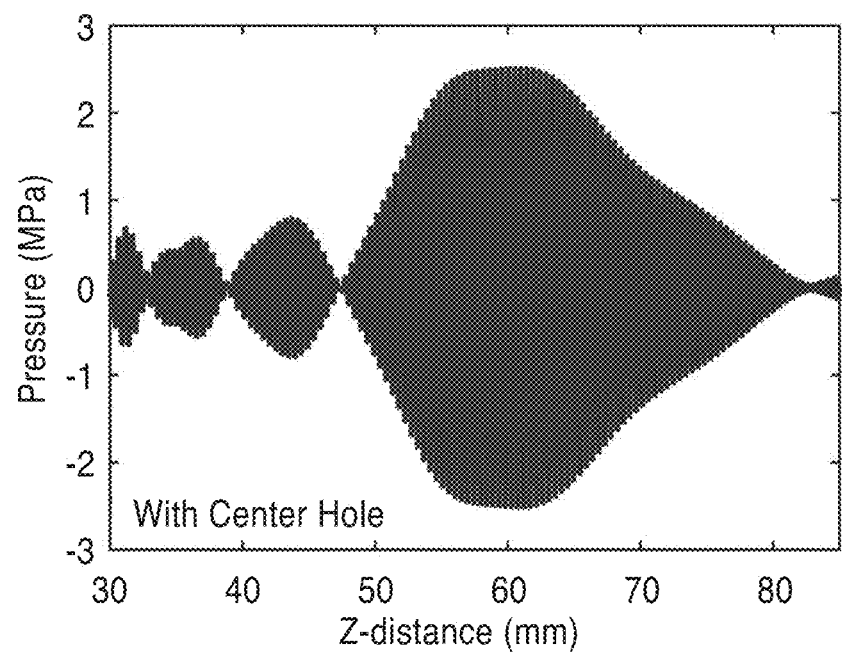
FIG. 7A and FIG. 7B show individual beam profiles both inner and outer transducer of FIG. 4B.
Figure 7B:
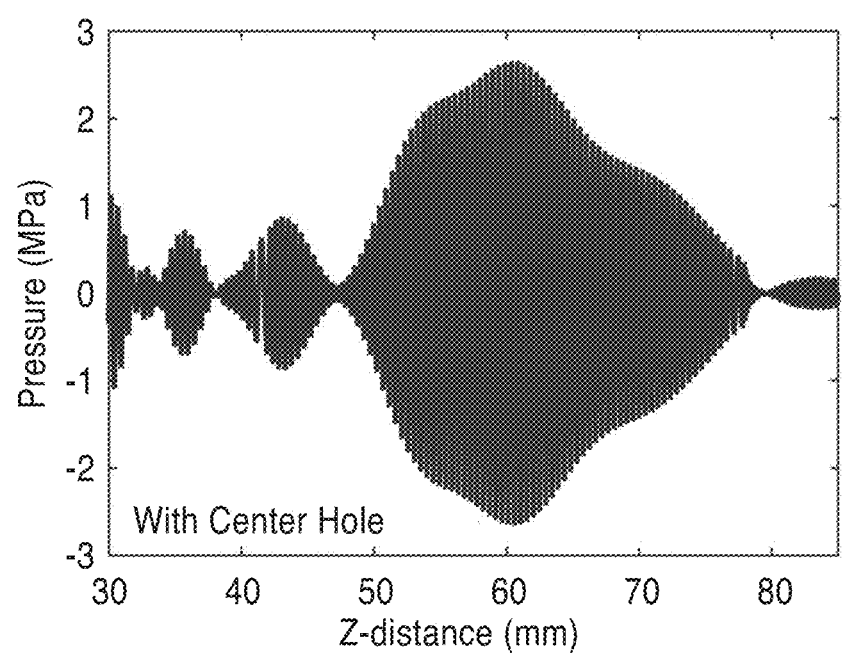
Figure 7C:
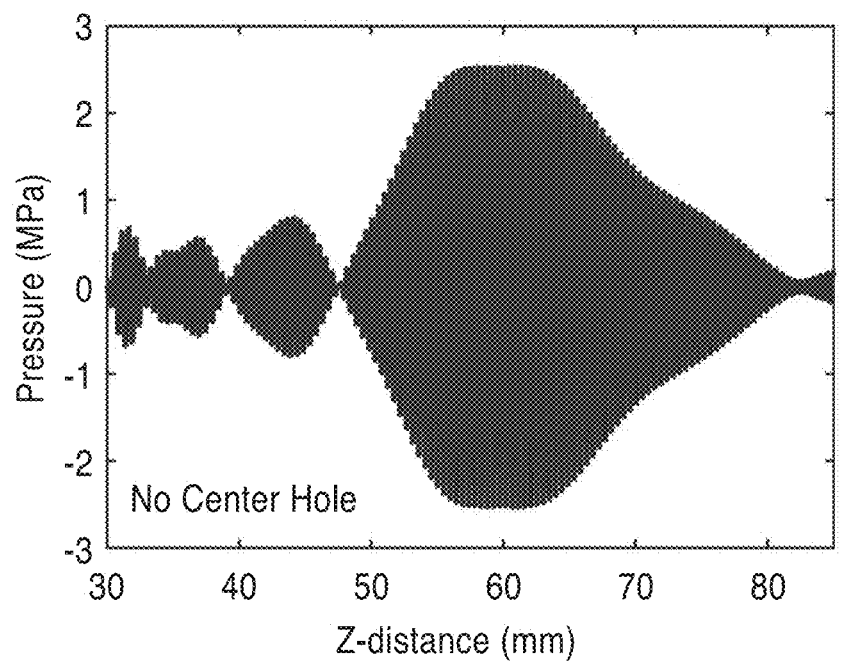
FIG. 7C and FIG. 7D show individual beam profiles both inner and outer transducer of FIG. 4A.
Figure 7D:
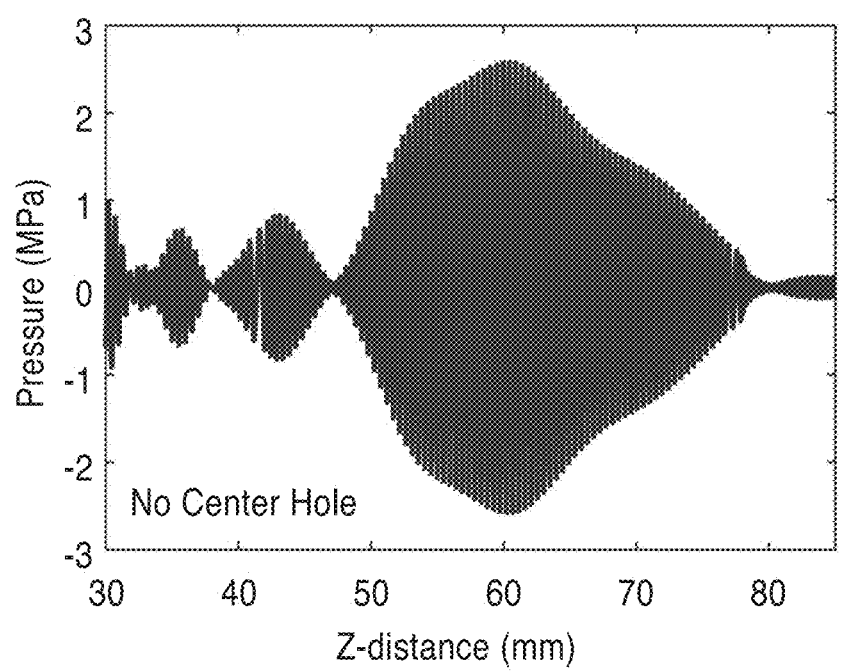

FIG. 7A through FIG. 7D shows a plot comparing beam profiles of the curved elements of FIG. 4A and FIG. 4B using a simulation for a compact in vivo VA system with COMSOL. FIG. 7A and FIG. 7B show individual beam profiles of the inner and outer transducer, respectively, of the confocal transducer 14*b* with center hole of FIG. 4B. FIG. 7C and FIG. 7D show individual beam profiles of the inner and outer transducer, respectively, of the confocal transducer 14*a* without center hole of FIG. 4A.

It was found that placement of a center hole 56 is expected to shift the focus spot by 0.7 mm and decrease the relative pressure by 1.0%, and that the overall beam pattern was unperturbed.

Figure 8:
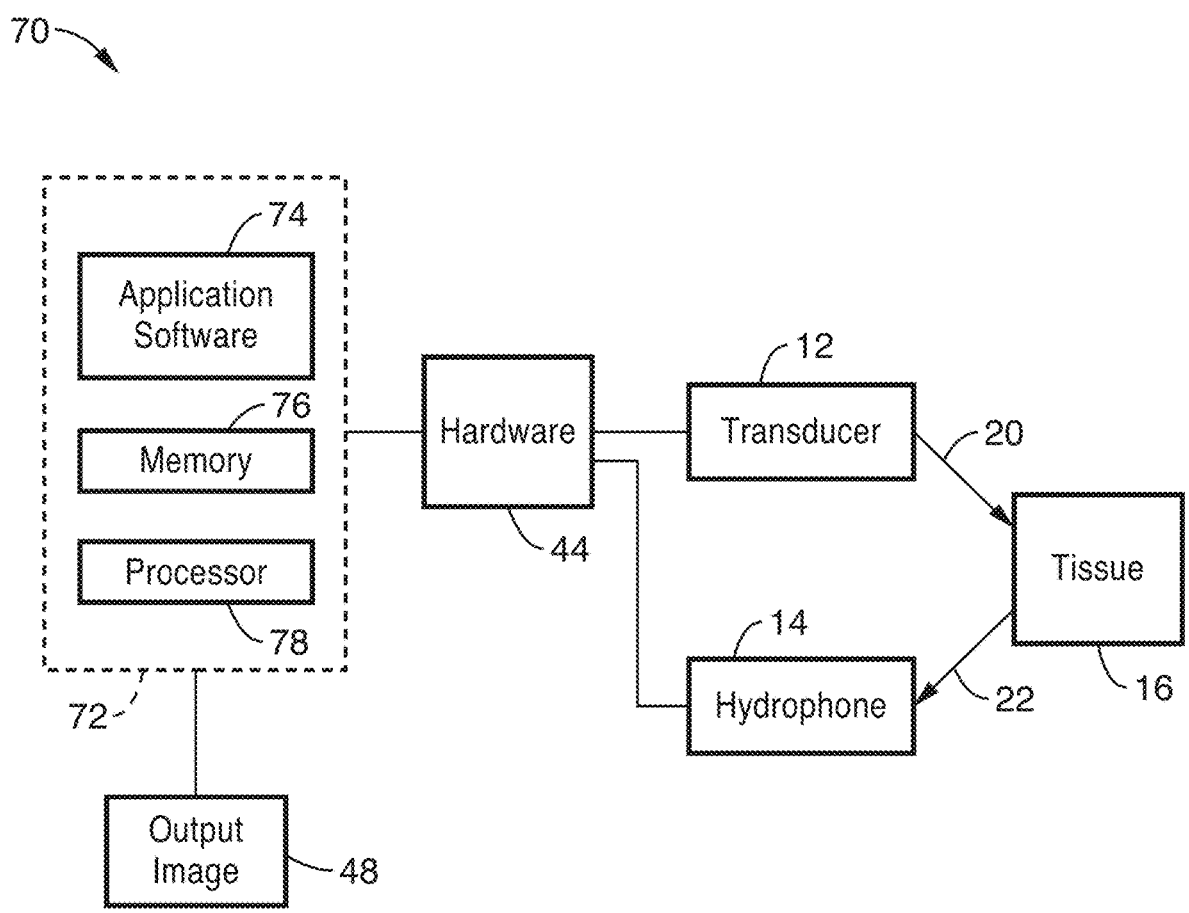
FIG. 8 shows high-level a schematic diagram of the VA system of FIG. 1 with processing components.

FIG. 8 shows high-level a schematic diagram of a VA system 70 with processing components. System 70 comprises a computing device 72 configured for executing application software 74 that is stored in memory 76 via a processor 78. Application software 74 may be configured for controlling transducer 12 and hardware 44 for generating the waves $f_1$ and $f_2$ (20) into tissue 16. Software 74 also may be configured to receive the output signal of hydrophone 14 (from waves 22), and process the signal to generate output image 48.

Hardware 44 further comprises a pair of splitters 26*a* and 26*b* that split the signals from signal generators 30*a* and 30*b*. Part of the signals are sent to a mixer 28, the output of which is fed to lock in amp 46 as a reference signal for lock-in and it goes through, wherein band pass filter is used in conjunction with output from mixer 28 to remove difference frequency (f1 and f2) from the LNA processed data 42 received from hydrophone 14. The application software 74 acts as a phase-sensitive spectrometer to detect the output signal. In a preferred embodiment, the images are generated by raster scanning the beam 20 throughout the field of view of tissue 16 through mechanical scanning or beam steering means (not shown), and processing the scanned data with application software 74 to generate an image map 48 of the mechanical (e.g. viscoelastic) response of the target 18 to the acoustic radiation force 20. Application software 74 may be configured so that pixel values are computed as the power at a particular harmonic or algebraic combination of powers at multiple harmonics.

In one embodiment, the application software 74 is configured to use acoustic as well as mechanical properties of the target tissue, such as elasticity and viscosity, which are not limited by the boundaries of the generated acoustic waves, and can provide absolute quantitative measurements of the target tissue. Application software 74 may further include a mathematical model based on the geometry, mechanical properties, and acoustic properties of the tissue in the phase and amplitude measurement to extract quantitative information from target.

2. Experiment and Results a. Sample Preparation

Tissue samples were procured from patients undergoing resection of squamous cell carcinomas (SCC). Resected samples included the tumor and all surrounding epithelial and mesenchymal structures isolated by the margin selection of the surgeon. Imaging was performed ex-vivo prior to tissue processing by the surgical pathologists. All imaging was performed within two hours of resection to ensure sample integrity representative of in-vivo conditions.

Ex-vivo tissue were sectioned and imaged using the acoustic imaging system 10 shown in FIG. 1. Photographs were taken of the specimens after being placed in the imaging system 10. The images of the specimens within the imaging system were then co-registered to the acoustic images via a non-reflective rigid affine transform using MATLAB 2013a (MathWorks, MA). The acoustic images were generated using false coloring.

b. Results

Multiple image sets at: $n_1*(\Delta f)$ and $n_2*(2*\Delta f)$ were been obtained of freshly resected head and neck squamous cell carcinoma that demonstrate significant contrast between tumor and normal tissue.

Figure 9A:
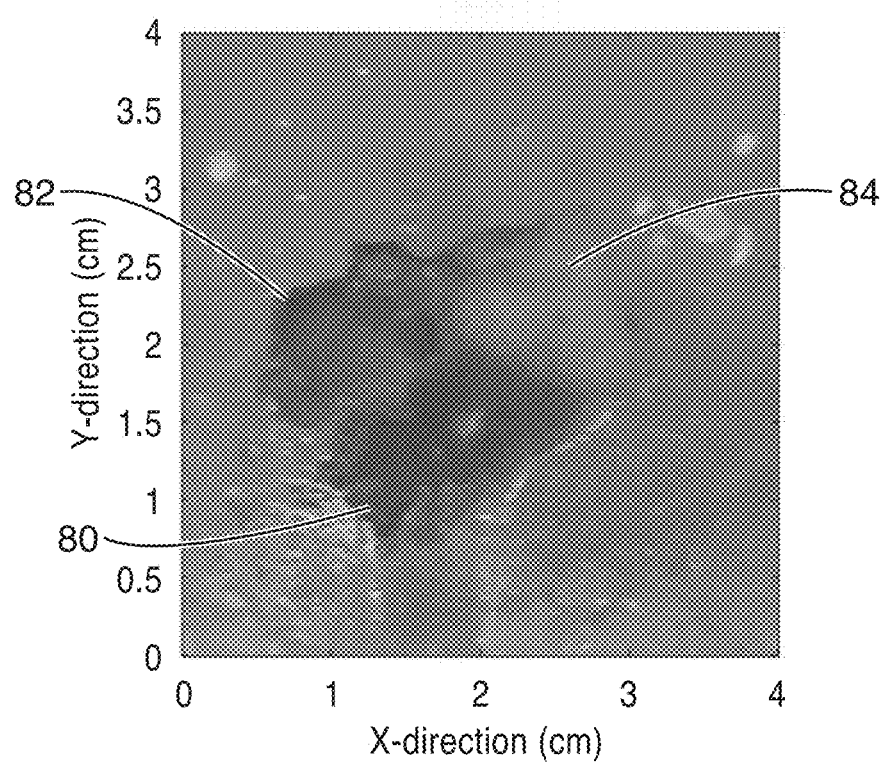
FIG. 9A illustrates a visible image of ex-vivo human parotid gland.
Figure 9B:
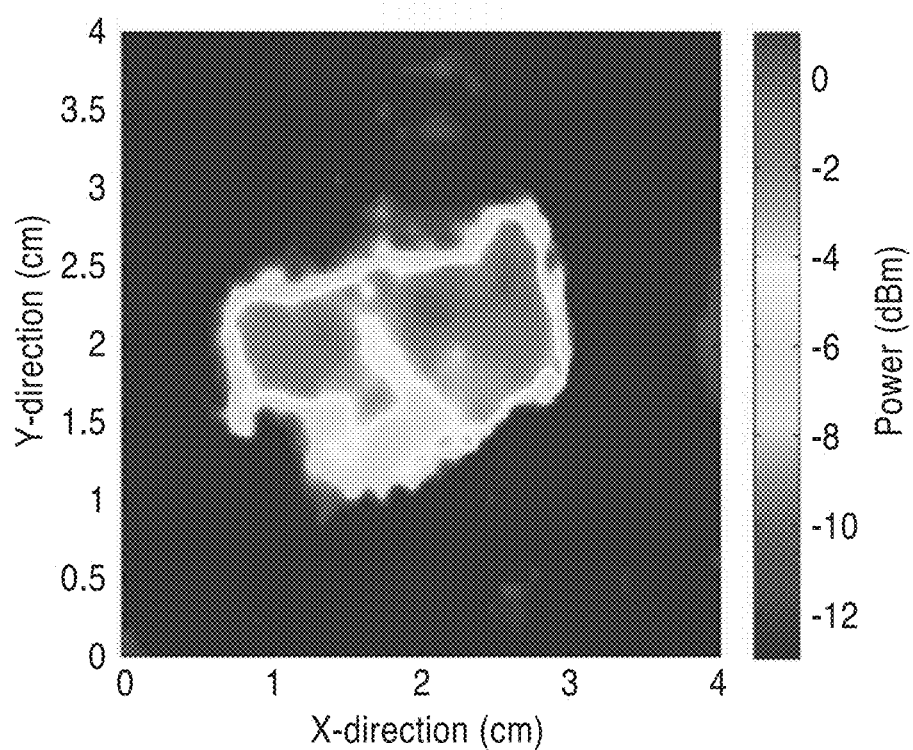
FIG. 9B illustrates the processed image of the parotid gland using the vibro-acoustography systems of the present description.

FIG. 9A illustrates a visible image of ex-vivo human parotid gland, and FIG. 9B illustrates the processed image of the parotid gland using the vibro-acoustography systems of the present description. The processed vibro-image of FIG. 9B shows the ability of the system to successfully distinguish between types of tissue (e.g. tumor tissue 80, healthy tissue 82, and fat tissue 84) within the sample based on the tissues' varying acoustic response to the low-frequency stress field.

Figure 10A:
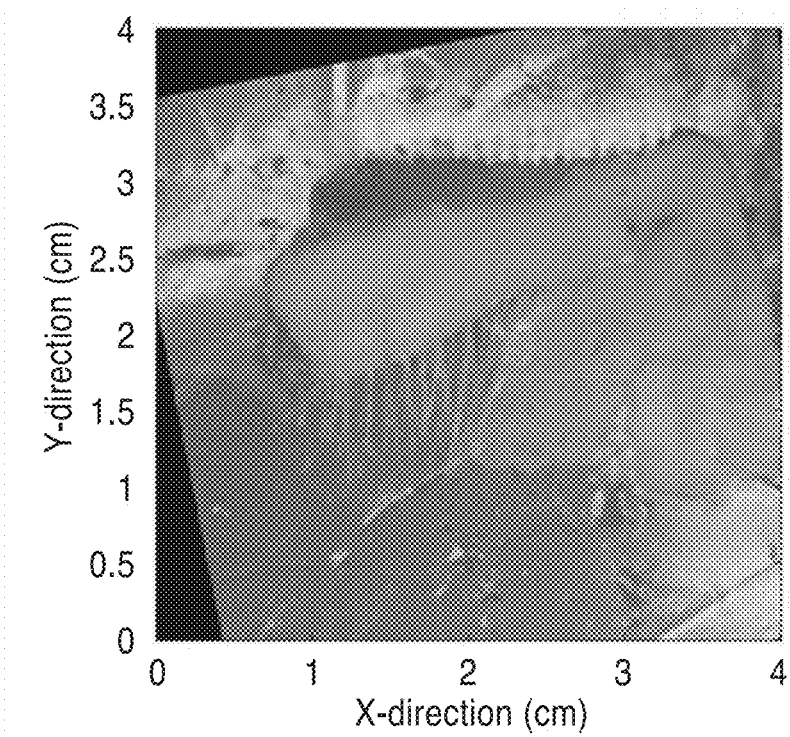
FIG. 10A illustrates a visible image of ex-vivo human scalp.
Figure 10B:
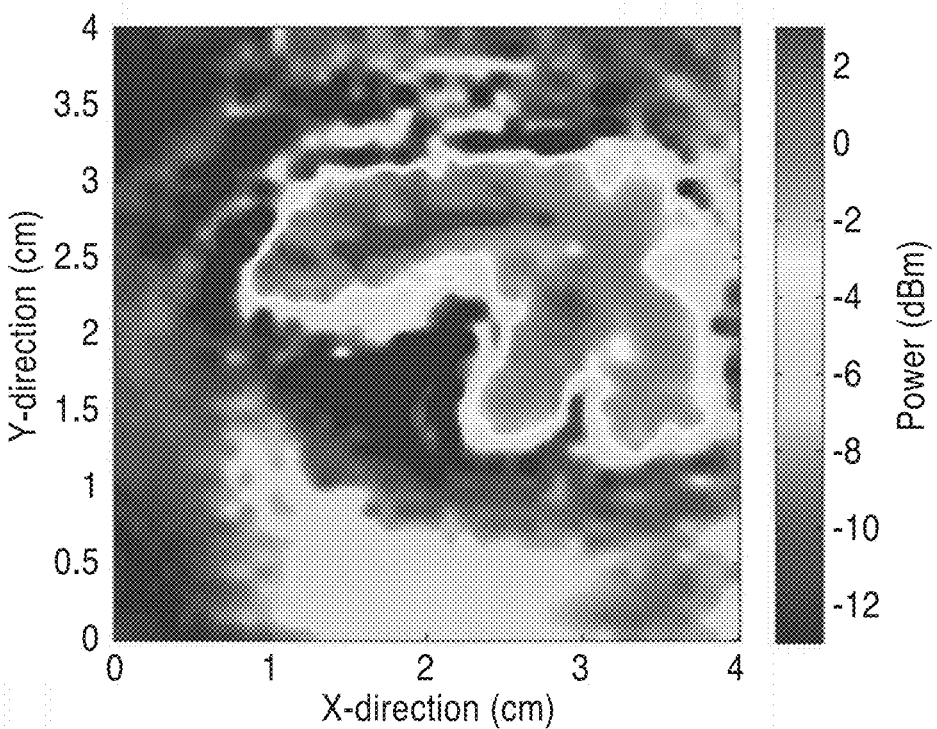
FIG. 10B illustrates the processed image of the scalp using the vibro-acoustography systems of the present description.
Figure 11A:
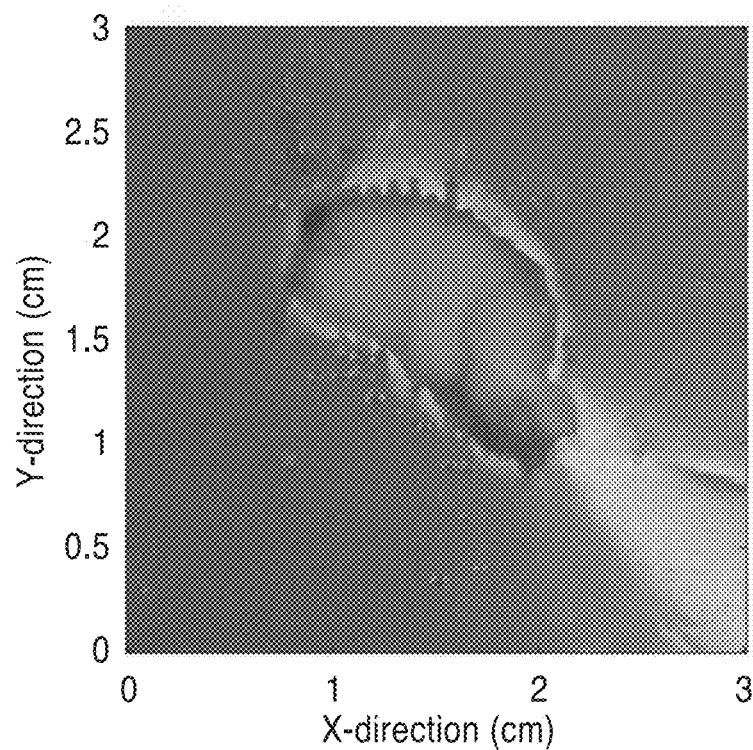
FIG. 11A illustrates a visible image of ex-vivo human mandible.
Figure 11B:
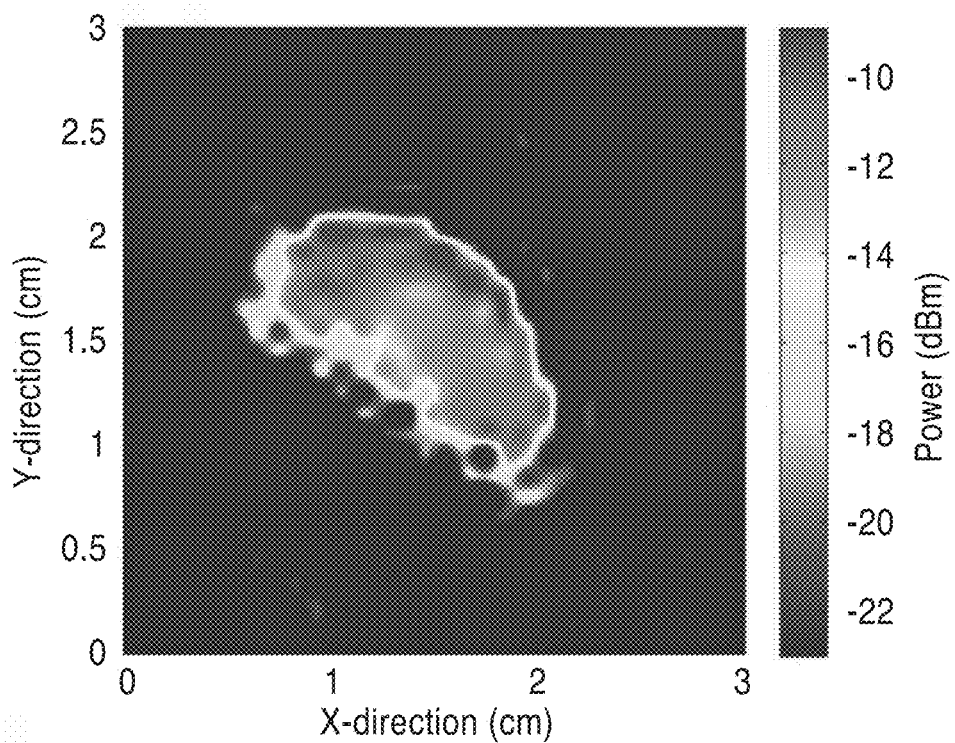
FIG. 11B illustrates the processed image of the human lip using the vibro-acoustography systems of the present description.
Figure 12A:
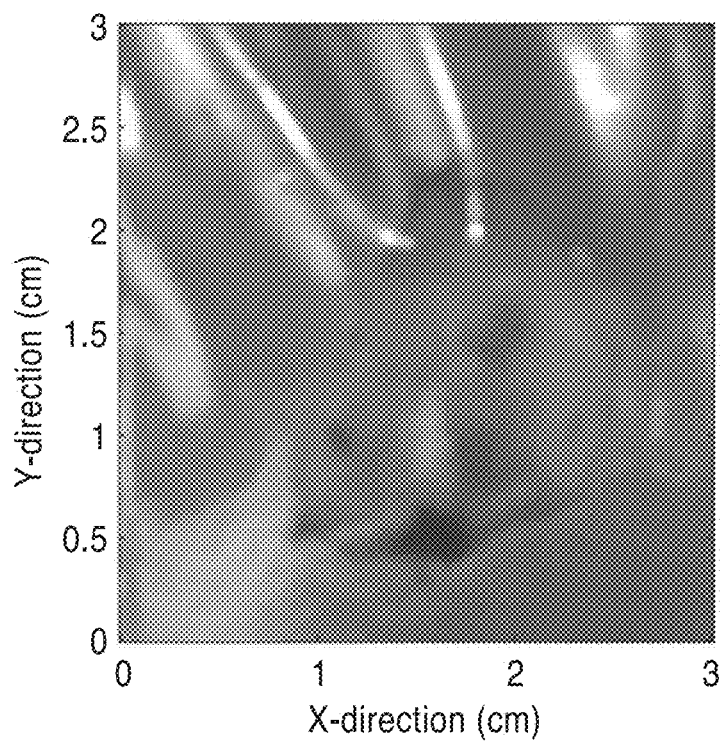
FIG. 12A illustrates a visible image of ex-vivo human mandible.
Figure 12B:
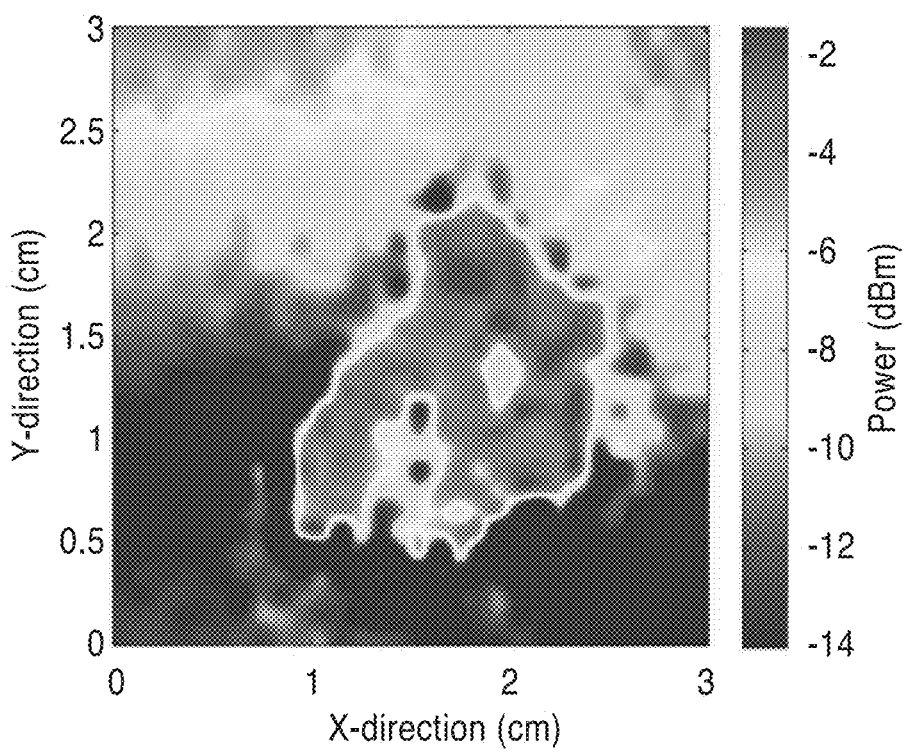
FIG. 12B illustrates the processed image of the human lip using the vibro-acoustography systems of the present description.

FIG. 10A illustrates a visible image of ex-vivo human scalp, and FIG. 10B illustrates the processed image of the scalp using the vibro-acoustography system 10 of the present description. FIG. 11A illustrates a visible image of ex-vivo human mandible, and FIG. 11B illustrates the processed image of the human lip using the vibro-acoustography system 10 of the present description. FIG. 12A illustrates a visible image of ex-vivo human mandible, and FIG. 12B illustrates the processed image of the human lip using the vibro-acoustography system 10 of the present description.

c. Frequency Characterization

Imaging results were acquired on custom fabricated tissue phantoms to further identify the ability of the vibro-acoustography system 10 to characterize tissue stiffness. The elasticity of the tissue can be extracted from the vibro-acoustographic signal spectrum of a volume of tissue interrogated with our Multi-frequency harmonic acoustography imaging system. Knowledge of interrogation volume, elasticity parameters and mechanical modeling enable the quantitative assessment of tissue elasticity.

As explained above, the VA system utilizes the inherent mechanical properties of biological materials to produce an image that corresponds to the response of the biological material to a low frequency ultrasonic acoustic wave in the low kHz range. Recent research has begun to show that biological materials differ in mechanical properties, particularly Young's Modulus (E) and Viscosity ($\eta$). Thus, different difference frequencies ($\Delta f$) must be explored to image various tissue mimicking phantoms (TMPs), as well as to obtain the mean power (dBm) of the emitted waves from each TMP.

Three types of TMPs (gelatin, agarose and Poly-Vinyl Alcohol (PVA)), were produced for VA imaging. Each phantom was imaged at 28 kHz, 38 kHz, and 48 kHz in order to distinguish a correspondence between each type of TMP, and a specific $\Delta f$ that produces the highest signal to noise ratio (SNR) while still maintaining effective contrast. All the TMP's were created by mixing powdered extracts with deionized water in a beaker in a water bath (~90° F.) to allow for cross linking of the polymers. The solutions were then placed out for two hours to solidify prior to imaging.

The TMPs all showed the highest mean power at the difference frequency of 48 kHz.

Figure 13A:
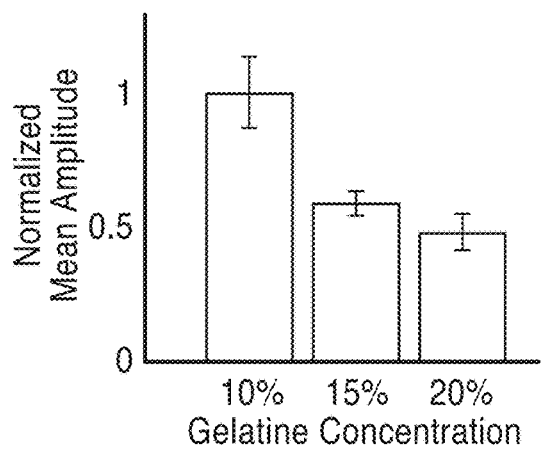
FIG. 13A through FIG. 13C are plots illustrating signal intensity vs. tissue stiffness for sample target materials comprising gelatin, agar and PVA, respectively.
Figure 13B:
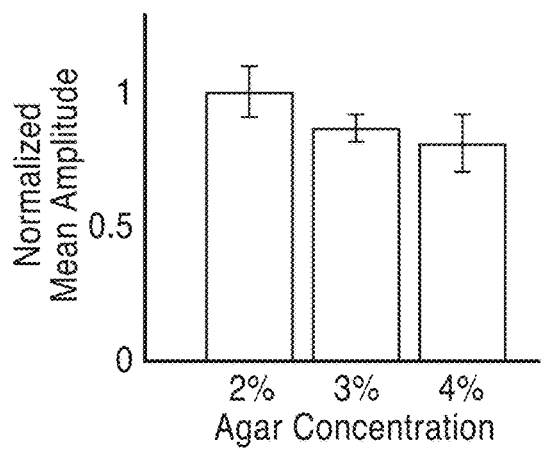
Figure 13C:
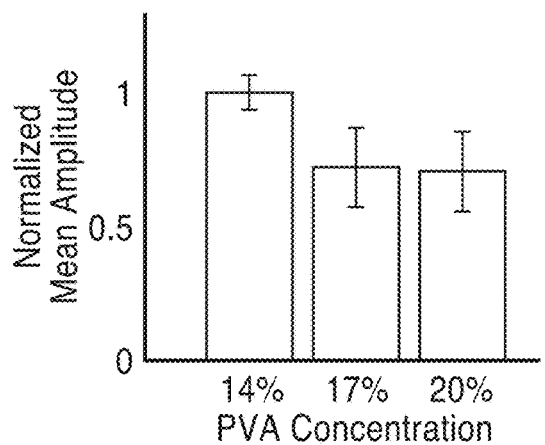

FIG. 13A, FIG. 13B, and FIG. 13C are plots illustrating signal intensity vs. tissue stiffness for sample target materials comprising gelatin, agar and PVA, respectively. Stiffness was measured as a function of the concentration of respective materials in the fabricated tissue. As seen in FIG. 13A through FIG. 14C, the signal intensity decreases as the stiffness increases among the same tissue types.

Figure 14:
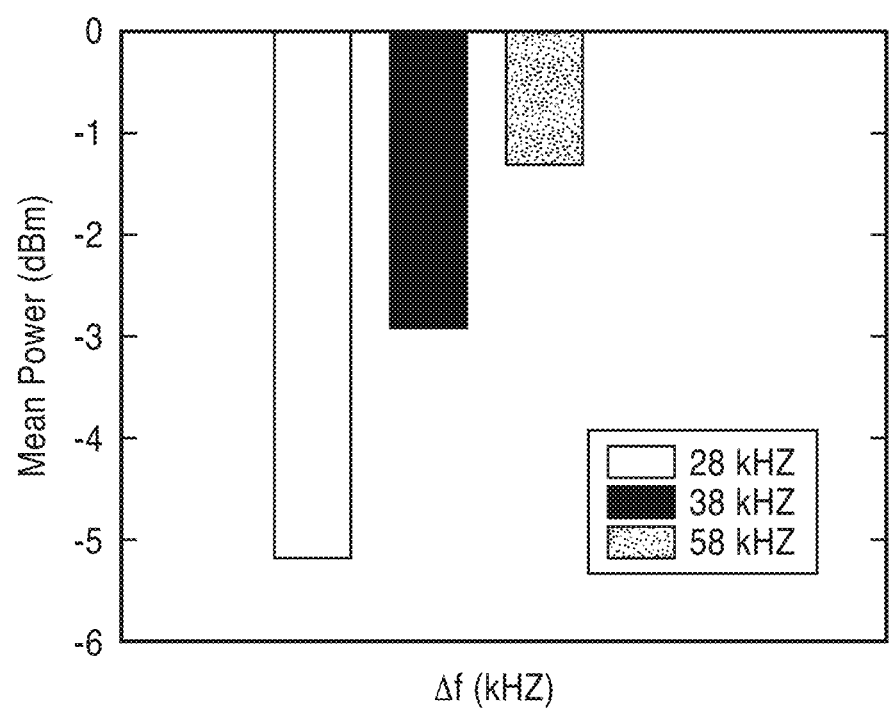
FIG. 14 is a plot of showing the mean power (dBm) of the emitted acoustic waves from a 3% by weight concentrated Agarose TMP at different Δf values using the VA system of the present description.

FIG. 14 shows a plot of the mean power (dBm) of the emitted acoustic waves from a 3% by weight concentrated Agarose TMP at different $\Delta f$ values, using the VA system 10 of the present description. Table 1 shows results of the relationship between imaging frequency and signal intensity. The mean power (dBm) for a 3% concentration of an Agarose TMP was used, showing that 48 kHz produced the highest mean power for that particular concentration of Agarose TMP. Moreover, as shown in Table 1, each type of TMP had the greatest mean intensity at this same $\Delta f$ (thus providing the highest image resolution and signal intensity), with an increase in mean power (dBm) as the $\Delta f$ increases. This phenomenon is due to the increased vibrations of the tissue, leading to a higher signal because of the higher $\Delta f$ acoustic wave. It is appreciated that even higher $\Delta f$ values may be used to distinguish the optimal difference frequency for each type of TMP, or target tissue where appropriate.

The above results have demonstrated the capability of VA system of the present description for target distinction and evaluation of phantoms and ex vivo surgical resection specimens. The system is preferably implemented as a compact VA system for in vivo intra-operative applications. The confocal transducer orientations described herein provide both versatile and reliable detection schemes. The system may be miniaturized by combining the transmitter and detector into one structure, with the center hole approximately the diameter of a needle hydrophone.

Additionally, the low operational frequency and high intrinsic dynamic range of the system of the present description allows processing to be performed by low power, integrated electronics, thus enabling implementation as a portable, hand-held device.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that the present disclosure encompasses multiple embodiments which include, but are not limited to, the following:

1. A method for performing multi-frequency harmonic acoustography for target identification and border detection within a target tissue, the method comprising: providing a focused confocal transducer having at least one piezoelectric element; focusing first and second ultrasonic waves at first and second frequencies from the transducer on the target tissue; wherein the first and second waves interfere at a focal plane within the target tissue such that the target tissue absorbs energy from the first and second waves and vibrates to emit a third acoustic wave within the target tissue; detecting the third acoustic wave with a hydrophone; and analyzing the third acoustic wave to evaluate one or more mechanical properties of the target tissue.

2. The method of any preceding or following embodiment, wherein the confocal transducer comprises a hydrophone positioned centrally within in the piezoelectric element.

3. The method of any preceding or following embodiment: wherein the confocal transducer comprises a first inner transducer disposed concentrically within a second outer transducer; wherein the first inner transducer emits the first wave at the first frequency and the second outer transducer emits the second wave at the second frequency; and wherein the hydrophone is positioned concentrically within a hole at the center of the first inner transducer.

4. The method of any preceding or following embodiment, wherein the confocal transducer comprises a curved array of transducers configured to electronically scan the target tissue, the hydrophone disposed within the array.

5. The method of any preceding or following embodiment, wherein the one or more mechanical properties of the target tissue comprise a boundary between malignant and normal tissue within the target tissue.

6. The method of any preceding or following embodiment: wherein evaluating one or more mechanical properties comprises analyzing harmonics generated by non-linear properties of the target tissue; and wherein the one or more mechanical properties of the target tissue are selected from the group consisting of: tissue type, size, location with adjacent tissue or physiologic or disease state.

7. The method of any preceding or following embodiment, wherein a spectral envelope comprising relative strengths of higher harmonics is used to create imaging contrast and unique identifying information associated with the target tissue.

8. The method of any preceding or following embodiment, wherein evaluating one or more mechanical properties of the target tissue comprises quantitative characterization of one or more material properties of the target tissue without reliance on reflection or attenuation of acoustic waves.

9. The method of any preceding or following embodiment: wherein the first and second waves cause the target tissue to vibrate at a difference frequency $\Delta f=|f1-f2|$, where f1 is the frequency of the first wave and f2 is the frequency of the second wave; and wherein detecting the third acoustic wave further comprises identifying variation of an acoustic yield of one or more harmonics of $\Delta f$.

10. The method of any preceding or following embodiment, wherein the acoustic yield of one or more harmonics of $\Delta f$ is calculated as an infinite sum of integer multiples of the fundamental: $n1*(\Delta f)+n2*(2*\Delta f)+n3*(3*\Delta f)+n4*(4*\Delta f)+\ldots$.

11. A system for performing multi-frequency harmonic acoustography for target identification and border detection, the system comprising: focused confocal transducer having at least one piezoelectric element; a hydrophone; and a signal processing circuit; the signal processing circuit comprising a computer hardware processor and a non-transitory memory storing instructions executable by the computer hardware processor which, when executed, perform steps comprising sending signals to the transducer to emit first and second ultrasonic waves at first and second frequencies from the transducer into a target tissue; wherein the first and second waves interfere at a focal plane within the target tissue such that the target tissue absorbs energy from the first and second waves and vibrates to emit a third acoustic wave within the target tissue; acquiring the third acoustic wave with a hydrophone; and analyzing the third acoustic wave to evaluate one or more mechanical properties of the target tissue.

12. The system of any preceding or following embodiment, wherein the confocal transducer comprises a hydrophone positioned centrally within in the piezoelectric element.

13. The system of any preceding or following embodiment: wherein the confocal transducer comprises a first inner transducer disposed concentrically within a second outer transducer; wherein the first inner transducer emits the first wave at the first frequency and the second outer transducer emits the second wave at the second frequency; and wherein the hydrophone is positioned concentrically within a hole at the center of the first inner transducer.

14. The system of any preceding or following embodiment, wherein the confocal transducer comprises a curved array of transducers configured to electronically scan the target tissue, the hydrophone disposed within the array.

15. The system of any preceding or following embodiment, wherein the one or more mechanical properties of the target tissue comprise a boundary between malignant and normal tissue within the target tissue.
16. The system of any preceding or following embodiment: wherein evaluating one or more mechanical properties comprises analyzing harmonics generated by non-linear properties of the target tissue; and wherein the one or more mechanical properties of the target tissue are selected from the group consisting of: tissue type, size, location with adjacent tissue or physiologic or disease state.
17. The system of any preceding or following embodiment, wherein a spectral envelope comprising relative strengths of higher harmonics is used to create imaging contrast and unique identifying information associated with the target tissue.
18. The system of any preceding or following embodiment, wherein evaluating one or more mechanical properties of the target tissue comprises quantitative characterization of one or more material properties of the target tissue without reliance on reflection or attenuation of acoustic waves.
19. The system of any preceding or following embodiment: wherein the first and second waves cause the target tissue to vibrate at a difference frequency $\Delta f=|f1-f2|$, where f1 is the frequency of the first wave and f2 is the frequency of the second wave; and wherein detecting the third acoustic wave further comprises identifying variation of an acoustic yield of one or more harmonics of $\Delta f$.
20. The system of any preceding or following embodiment, wherein the acoustic yield of one or more harmonics of $\Delta f$ is calculated as an infinite sum of integer multiples of the fundamental: $n1*(\Delta f)+n2*(2*\Delta f)+n3*(3*\Delta f)+n4*(4*\Delta f)+ \ldots$.
21. The system of any preceding or following embodiment, further comprising: one or more pulse generators for and one or more amplifiers for generating the first and second waves as unmodulated continuous wave (CW) ultrasonic beams at the first and second frequencies in the low MHz range; wherein the confocal transducer comprises a first inner transducer disposed concentrically within a second outer transducer; wherein the first and second waves are input into the confocal transducer with the first wave coupled to the inner transducer and the second wave coupled to the outer transducer to create two converging beams that overlap at the target tissue.
22. The system of any preceding or following embodiment, further comprising a band pass filter used to remove the first and second waves from the acquired signal.
23. A method for performing multi-frequency harmonic acoustography for target identification and border detection, the method comprising: providing a focused confocal transducer having a piezoelectric element and a hydrophone positioned centrally in the piezoelectric element; focusing ultrasonic waves at first and second frequencies from the transducer on a target of interest; wherein the two waves interfere at a focal plane within the target to generate a third acoustic wave and wherein the target absorbs energy and emits its own unique vibration at the difference frequency ($\Delta f$) as well as its harmonics; recording the unique vibration with the hydrophone; and ascertaining mechanical properties of the target through detection and analysis of the third acoustic wave.
24. The method of any preceding or following embodiment, wherein analysis of the third acoustic wave include analysis of the harmonics.
25. The method of any preceding or following embodiment, wherein the mechanical properties of the target are selected from the group consisting of convolution of tissue type, size, and adjacent tissue and unique to the physiologic or disease state of the tissue of interest.
26. A system for performing multi-frequency harmonic acoustography for target identification and border detection, the system comprising: a focused confocal transducer having a piezoelectric element and a hydrophone positioned centrally in the piezoelectric element; a signal processing circuit; the signal processing circuit comprising a computer hardware processor and a non-transitory memory storing instructions executable by the computer hardware processor which, when executed, perform steps comprising: causing the transducer to emit ultrasonic waves at first and second frequencies from the transducer on a target of interest; wherein the two waves interfere at a focal plane within the target to generate a third acoustic wave and wherein the target absorbs energy and emits its own unique vibration at the difference frequency ($\Delta f$) as well as its harmonics; recording the unique vibration with the hydrophone; and ascertaining mechanical properties of the target through detection and analysis of the third acoustic wave.
27. The system of any preceding or following embodiment, wherein analysis of the third acoustic wave include analysis of the harmonics.
28. The system of any preceding or following embodiment, wherein the mechanical properties of the target are selected from the group consisting of convolution of tissue type, size, and adjacent tissue and unique to the physiologic or disease state of the tissue of interest.
29. A method for performing multi-frequency harmonic acoustography for target identification and border detection, the method comprising: providing a focused confocal transducer having a piezoelectric element and a hydrophone positioned centrally in the piezoelectric element; focusing ultrasonic waves at first and second frequencies from the transducer on a target of interest; wherein the two waves interfere at a focal plane within the target to generate a third acoustic wave and wherein the target absorbs energy and emits its own unique vibration at the difference frequency ($\Delta f$) as well as its harmonics; recording the unique vibration with the hydrophone; and ascertaining mechanical properties of the target through detection and analysis of the third acoustic wave.
30. The method of any preceding or following embodiment, wherein analysis of the third acoustic wave include analysis of the harmonics.
31. The method of any preceding or following embodiment, wherein the mechanical properties of the target are selected from the group consisting of convolution of tissue type, size, and adjacent tissue and unique to the physiologic or disease state of the tissue of interest.
32. A system for performing multi-frequency harmonic acoustography for target identification and border detection, the system comprising: a focused confocal transducer having a piezoelectric element and a hydrophone positioned centrally in the piezoelectric element;

a signal processing circuit; the signal processing circuit comprising a computer hardware processor and a non-transitory memory storing instructions executable by the computer hardware processor which, when executed, perform steps comprising: causing the transducer to emit ultrasonic waves at first and second frequencies from the transducer on a target of interest; wherein the two waves interfere at a focal plane within the target to generate a third acoustic wave and wherein the target absorbs energy and emits its own unique vibration at the difference frequency ($\Delta f$) as well as its harmonics; recording the unique vibration with the hydrophone; and ascertaining mechanical properties of the target through detection and analysis of the third acoustic wave.

33. The system of any preceding or following embodiment, wherein analysis of the third acoustic wave include analysis of the harmonics.

34. The system of any preceding or following embodiment, wherein the mechanical properties of the target are selected from the group consisting of convolution of tissue type, size, and adjacent tissue and unique to the physiologic or disease state of the tissue of interest.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Relationship Between Imaging Frequency And Signal Intensity

|  | Power at 28 kHz | Power at 38 kHz | Power at 48 kHz |
| --- | --- | --- | --- |
| Gelatin 15% | −8.05 | −5.88 | −5.34 |
| Agar 3% | −5.24 | −2.99 | −1.32 |
| PVA 17% | −19.37 | −16.65 | −16.84 |

What is claimed is:

1. A method for performing multi-frequency harmonic acoustography for target identification and border detection within a target tissue, the method comprising:
   providing a focused confocal transducer having at least one piezoelectric element;
   focusing first and second ultrasonic waves at first and second frequencies from the transducer on the target tissue;
   wherein the first and second waves interfere at a focal plane within the target tissue such that the target tissue absorbs energy from the first and second waves and vibrates to emit a third acoustic wave within the target tissue;
   detecting the third acoustic wave with a hydrophone; and
   analyzing the third acoustic wave to evaluate one or more mechanical properties of the target tissue by analyzing harmonics generated by non-linear properties of the target tissue, wherein a spectral envelope comprising relative strengths of higher harmonics is used to create imaging contrast and unique identifying information associated with the target tissue; and
   wherein the one or more mechanical properties of the target tissue are selected from the group consisting of: tissue type, size, location with adjacent tissue or physiologic or disease state.

2. The method of claim 1, wherein the confocal transducer comprises a hydrophone positioned centrally within in the piezoelectric element.

3. The method of claim 2:
   wherein the confocal transducer comprises a first inner transducer disposed concentrically within a second outer transducer;
   wherein the first inner transducer emits the first wave at the first frequency and the second outer transducer emits the second wave at the second frequency; and
   wherein the hydrophone is positioned concentrically within a hole at the center of the first inner transducer.

4. The method of claim 2, wherein the confocal transducer comprises a curved array of transducers configured to electronically scan the target tissue, the hydrophone disposed within the array.

5. The method of claim 1, wherein the one or more mechanical properties of the target tissue comprise a boundary between malignant and normal tissue within the target tissue.

6. The method of claim 1, wherein evaluating one or more mechanical properties of the target tissue comprises quantitative characterization of one or more material properties of the target tissue without reliance on reflection or attenuation of acoustic waves.

7. A system for performing multi-frequency harmonic acoustography for target identification and border detection, the system comprising:
   a focused confocal transducer having at least one piezoelectric element;
   a hydrophone; and
   a signal processing circuit;
   the signal processing circuit comprising a computer hardware processor and a non-transitory memory storing instructions executable by the computer hardware processor which, when executed, perform steps comprising:
   sending signals to the transducer to emit first and second ultrasonic waves at first and second frequencies from the transducer into a target tissue;
   wherein the first and second waves interfere at a focal plane within the target tissue such that the target tissue absorbs energy from the first and second waves and vibrates to emit a third acoustic wave within the target tissue;
   analyzing the third acoustic wave to evaluate one or more mechanical properties of the target tissue by analyzing harmonics generated by non-linear properties of the target tissue, wherein a spectral envelope comprising relative strengths of higher harmonics is used to create imaging contrast and unique identifying information associated with the target tissue;
   wherein the one or more mechanical properties of the target tissue are selected from the group consisting of: tissue type, size, location with adjacent tissue or physiologic or disease state.

8. The system of claim 7, wherein the confocal transducer comprises a hydrophone positioned centrally within the piezoelectric element.

9. The system of claim 8:
   wherein the confocal transducer comprises a first inner transducer disposed concentrically within a second outer transducer;
   wherein the first inner transducer emits the first wave at the first frequency and the second outer transducer emits the second wave at the second frequency; and
   wherein the hydrophone is positioned concentrically within a hole at the center of the first inner transducer.

10. The system of claim 8, wherein the confocal transducer comprises a curved array of transducers configured to electronically scan the target tissue, the hydrophone disposed within the array.

11. The system of claim 7, wherein the one or more mechanical properties of the target tissue comprise a boundary between malignant and normal tissue within the target tissue.

12. The system of claim 7, wherein evaluating one or more mechanical properties of the target tissue comprises quantitative characterization of one or more material properties of the target tissue without reliance on reflection or attenuation of acoustic waves.

13. The system of claim 7, further comprising:
   one or more pulse generators for and one or more amplifiers for generating the first and second waves as unmodulated continuous wave (CW) ultrasonic beams at the first and second frequencies in the low MHz range;
   wherein the confocal transducer comprises a first inner transducer disposed concentrically within a second outer transducer;
   wherein the first and second waves are input into the confocal transducer with the first wave coupled to the inner transducer and the second wave coupled to the outer transducer to create two converging beams that overlap at the target tissue.

14. The system of claim 13, further comprising a band pass filter used to remove the first and second waves from the acquired signal.

* * * * *